United States Patent
Hameed et al.

(10) Patent No.: US 11,715,558 B2
(45) Date of Patent: Aug. 1, 2023

(54) SYSTEMS AND METHODS FOR DETECTING DEFECTS IN MEDICAL DEVICES

(71) Applicants: Salmaan Hameed, San Jose, CA (US); Stephen Budill, San Francisco, CA (US); Michael S. Humason, Newbury Park, CA (US)

(72) Inventors: Salmaan Hameed, San Jose, CA (US); Stephen Budill, San Francisco, CA (US); Michael S. Humason, Newbury Park, CA (US)

(73) Assignee: BH2 INNOVATIONS INC., Newbury Park, CA (US)

( * ) Notice: Subject to any disclaimer, the term of this patent is extended or adjusted under 35 U.S.C. 154(b) by 0 days.

(21) Appl. No.: 16/912,337

(22) Filed: Jun. 25, 2020

(65) Prior Publication Data
US 2020/0405134 A1    Dec. 31, 2020

Related U.S. Application Data

(60) Provisional application No. 62/866,535, filed on Jun. 25, 2019.

(51) Int. Cl.
*A61B 1/00* (2006.01)
*G16H 40/40* (2018.01)
(Continued)

(52) U.S. Cl.
CPC ......... *G16H 40/40* (2018.01); *A61B 1/00013* (2013.01); *A61B 1/00029* (2013.01);
(Continued)

(58) Field of Classification Search
CPC . A61B 1/045; A61B 1/00009; A61B 1/00013; A61B 1/00029; A61B 1/00039;
(Continued)

(56) References Cited

U.S. PATENT DOCUMENTS

| | | | |
|---|---|---|---|
| 2006/0030891 A1* | 2/2006 | Saltzstein | G16Z 99/00 607/32 |
| 2011/0080588 A1* | 4/2011 | Segall | G01N 21/954 356/445 |

(Continued)

OTHER PUBLICATIONS

Barakat, Monique T., et al. "Scoping the scope: endoscopic evaluation of endoscope working channels with a new high-resolution inspection endoscope (with video)." Gastrointestinal endoscopy 88.4 (2018): 601-611.*

*Primary Examiner* — Anh Tuan T Nguyen
*Assistant Examiner* — Sung Ham
(74) *Attorney, Agent, or Firm* — Ansari Katiraei LLP; Arman Katiraei; Sadiq Ansari

(57) ABSTRACT

A detection system is adapted to perform methods for detecting defects in medical devices, during a reprocessing procedure, for example. The detection system may utilize computer-implemented instructions to determine the presence and nature of the defects, whether biological or mechanical, for example. The computer-implemented instructions may be adapted to include artificial intelligence and/or machine learning algorithms, and to process image data from digital inspection camera systems or proprietary camera systems. Upon identification of a defect present in a medical device, the detection system may notify users of the presence of the defect, as well as provide further recommended action to be taken regarding the medical device, if desirable, reducing potential instrument failure, patient injury or death. The disclosed detection system may be integrated into existing disinfection and sterilization systems currently used in medical facilities, such as hospitals and surgery centers, for example.

17 Claims, 10 Drawing Sheets

(51) Int. Cl.
*A61B 1/045* (2006.01)
*G16H 40/63* (2018.01)

(52) U.S. Cl.
CPC .......... *A61B 1/00147* (2013.01); *A61B 1/045* (2013.01); *G16H 40/63* (2018.01); *A61B 1/000096* (2022.02)

(58) Field of Classification Search
CPC .......... A61B 1/00147; A61B 1/000096; A61B 1/00055; A61B 1/00057; A61B 1/00059; A61B 1/00062; A61B 6/58; A61B 6/581; A61B 6/582; A61B 6/586; G16H 40/40; G16H 40/63; G16H 40/60; G16H 40/57; G01N 21/93; G01N 21/94; G01N 21/954; G06T 7/0004
See application file for complete search history.

(56) References Cited

U.S. PATENT DOCUMENTS

| | | | | |
|---|---|---|---|---|
| 2016/0331213 | A1* | 11/2016 | Kim | A61B 5/6898 |
| 2017/0135558 | A1* | 5/2017 | Choi | A61B 1/00057 |
| 2018/0102189 | A1* | 4/2018 | Hosoi | G16H 40/40 |
| 2018/0286510 | A1* | 10/2018 | Kwan | G06Q 10/20 |
| 2018/0353061 | A1* | 12/2018 | Tanaka | A61B 1/05 |
| 2019/0038791 | A1* | 2/2019 | Gerrans | B08B 3/08 |
| 2019/0082943 | A1* | 3/2019 | Mitsunaga | A61B 1/00009 |
| 2019/0224357 | A1* | 7/2019 | Sundet | A61B 1/0057 |
| 2021/0098123 | A1* | 4/2021 | Endo | A61B 1/00059 |
| 2021/0386278 | A1* | 12/2021 | Jackson | A61B 90/98 |

* cited by examiner

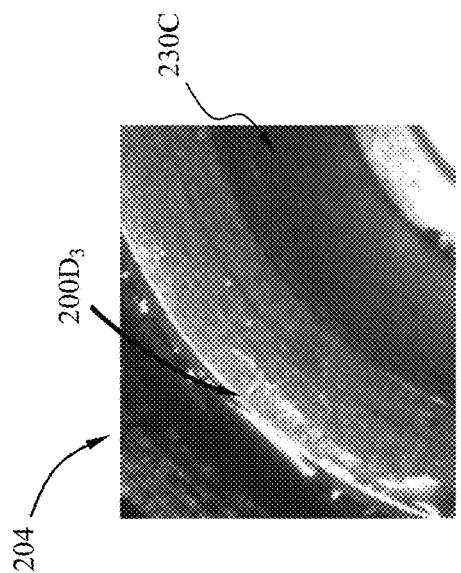
FIG. 2C
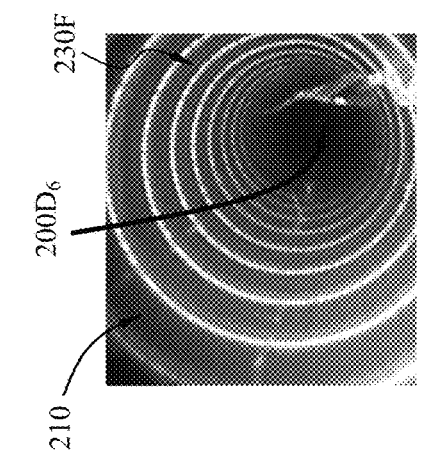
FIG. 2F
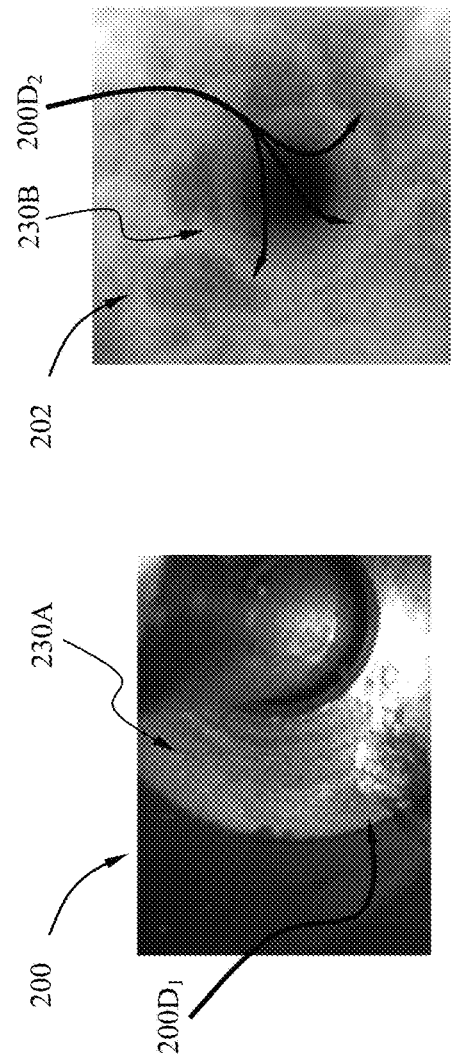
FIG. 2B
FIG. 2E
FIG. 2A
FIG. 2D

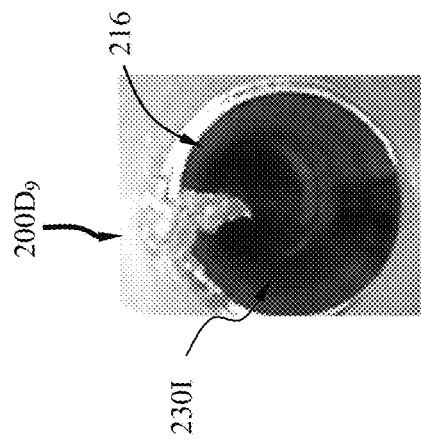
FIG. 2I
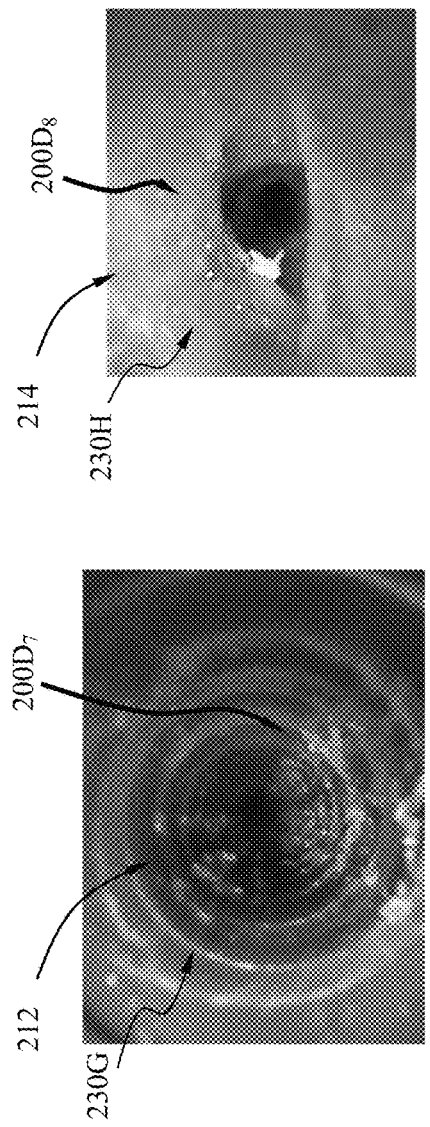
FIG. 2G
FIG. 2H
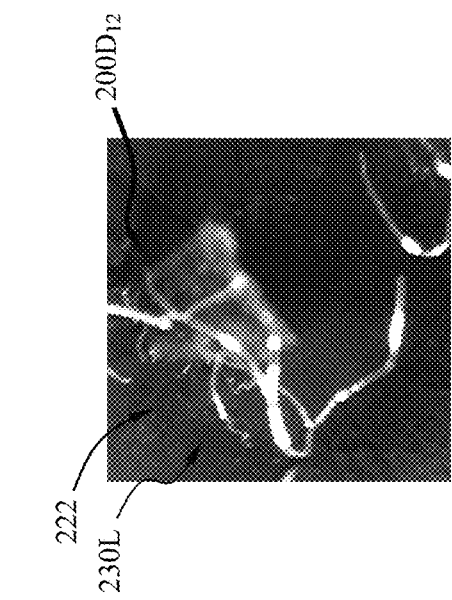
FIG. 2L
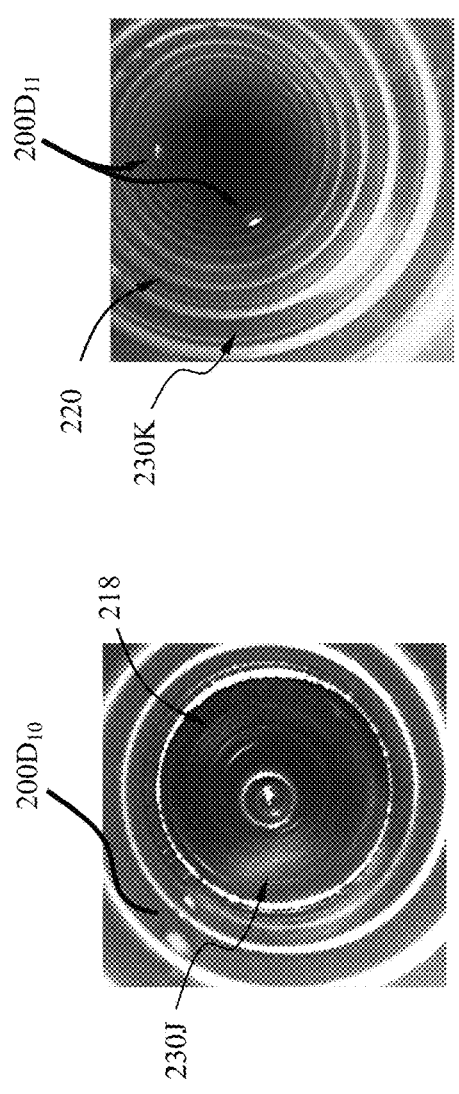
FIG. 2J
FIG. 2K

SYSTEMS AND METHODS FOR DETECTING DEFECTS IN MEDICAL DEVICES

This application claims priority to U.S. Provisional Application Ser. No. 62/866,535, entitled "Systems and Methods for Detecting Defects in Medical Devices," filed Jun. 25, 2019, the application incorporated herein by reference in its entirety.

BACKGROUND

Medical devices, such as colonoscopes, laparoscopes, and arthroscopes, are used in the performance of over 18 million medical procedures in the United States every year. After each medical procedure the associated medical device is reprocessed for use in another upcoming procedure. A reprocessing procedure, for example, may include a cleaning and sterilization of the medical device, followed by a visual inspection of the various working channels of the medical device to determine whether a defect still exists. The defect may be a biological defect, for example, the defect being bio-burden within a portion of a working channel of the medical device. Examples of bio-burden may include, but are not limited to, biological fluids, such as blood, biological tissues, and/or various forms of bacteria. Alternatively, the defect may be mechanical in nature. For example, the medical device itself may be excessively worn or damaged during use. The mechanical defect may be a break or crack, or other mechanical failure in the physical structure of the medical device, which may lead to the undesirable transmission of bio-burden or other non-biological material between the working channel of the medical device and a patient's body cavity. Last, the defect may be a portion of non-biological material originating from the medical device itself, or a working device positioned within the corresponding working channel during the performance of a medical procedure.

If one or more such defects are present but are not discovered or observed during the reprocessing procedure the one or more defects may contaminate a patient in a future medical procedure. These undiscovered defects may be a primary source of healthcare-acquired infections, the reprocessed medical devices being a source of hospital borne infections, leading to undesirable patient injury or even death. Some studies have found that up to 70% of reprocessed medical devices are contaminated with various forms of bio-burden.

In an attempt to limit the biological and mechanical defects found in medical devices after the performance of a medical procedure, and as may be required for compliance with various standards organizations, healthcare facilities are increasingly purchasing inspection systems to provide an inspection technician visual access to various structures of a medical device, including the internal working channels. Such inspection technicians, however, may not be highly educated or motivated and may be under tremendous pressure to complete medical device inspections in a timely manner so the associated medical devices may be utilized in upcoming medical procedures. Present visual inspection techniques performed by inspection technicians, however, are highly dependent on human interaction and judgement, and are subject to human error, which may lead to errors in defect detection and, ultimately, patient injury or death due to the presence of the defect, whether biological or mechanical, and subsequent contamination of the patient.

Additionally, direct visual inspection systems allow users early detection of mechanical defects that may lead to medical instrument failure. Medical device failure during medical procedures is not uncommon and may cause procedural interruptions lasting several minutes or more. The ability to predict failure through early detection of mechanical defects, therefore, has value to medical providers and patients.

Accordingly, there is a need for a detection system adapted to determine the presence of defects in medical devices, and to identify the nature of such defects. A detection system to provide for a more reliable reprocessing procedure to minimize human interaction, minimize variations due to human judgement, and increase user notifications is desirable, such notifications including whether a defect is present and whether the defect is a biological defect or a mechanical defect. A determination by the detection system whether the medical device should be reprocessed once again or removed from service is also desired. Further, a detection system that can integrate into existing disinfection and sterilization systems currently utilized by medical facilities in reprocessing procedures is also desirable.

BRIEF SUMMARY

Consistent with the present disclosure, a detection system is adapted to perform methods for detecting defects in medical devices, during a reprocessing procedure, for example. The detection system may utilize computer-implemented instructions to determine the presence and nature of the defects, whether biological or mechanical, for example. The computer-implemented instructions may be adapted to include artificial intelligence and/or machine learning algorithms, and process image data from currently available digital inspection camera systems or proprietary camera systems, as desired. Upon identification of a defect present in a medical device, the detection system may notify users of the presence of the defect, as well as provide further recommended action to be taken regarding the medical device, if desirable, reducing potential instrument failure, patient injury or death. The disclosed detection system may be integrated into existing disinfection and sterilization systems currently used in medical facilities, such as hospitals and surgery centers, for example.

In one aspect, a method for detection of defects of a medical device may include obtaining procedural data related to the medical device, positioning a detection scope within the medical device, acquiring one or more images at a current location of the detection scope, advancing the detection scope within the medical device, identifying one or more defects within the medical device, and updated the procedural data related to the medical device. In certain embodiments, the procedural data may include one or more of a medical instrument record, a service record, and a meta data record. Positioning the detection scope may include positioning the detection scope within a working channel of a medical device. A determination whether an end of the working channel is reached by the distal tip of the detection scope may be determined.

In certain embodiments, the steps of acquiring the plurality of images, advancing the detection scope, identifying defect, and determining whether the end of the working channel of the medical device has been reached may be repeated one or more times. Once the end of the working channel is reached by the distal tip of the detecting scope procedural data may be updated.

In some embodiments, identifying one or more defects may include determining a location for each of the one or more defects. Determining the location for each of the one or more defects may include performing an optical flow analysis. Determining the location for each of the one or more defects may further include measuring an acceleration of the distal tip of the detection scope. In some embodiments, determining the location for each of the one or more defects may include measuring a ratio between the rotational movement of the motor and the linear movement of the detection scope.

In another aspect, a device for detection of a defect of a medical device may include an imaging device configured to acquire image data, a processor coupled to the imaging device, the processor configured to analyze image data received from the imaging device, and a data source coupled to the processor, the data source may be adapted to store image data acquired by the imaging device, among other things.

In some embodiments, the device may further comprise an input device coupled to the imaging device and the processor, the input device communicating image data between the imaging device and the processor, the input device may be adapted to control the characteristics of the image device. The data source may include a meta data record, a medical instrument record, and a service data record.

In some embodiments, the input device may be configured to couple to the imaging device wirelessly, and the input device may be configured to couple to the processor wirelessly. The input device may also be configured to process image data prior to passing the image data on to the processor.

BRIEF DESCRIPTION OF THE DRAWINGS

Reference will be made to embodiments of the disclosure, examples of which may be illustrated in the accompanying figures. These figures are intended to be illustrative, not limiting. Although certain aspects of the embodiments are generally described in the context of these embodiments, it should be understood that such description is not intended to limit the scope to these particular embodiments. In the drawings.

DETAILED DESCRIPTION

Systems and methods for detecting defects in medical devices are disclosed, such defects being biological or mechanical, for example. The methods described herein may be computer-implemented methods comprising processor executable instructions stored in the memory of a controller or processor, or otherwise a memory accessible by the controller or processor, whether local or remote.

The following description is set forth for explanation to provide an understanding of the various embodiments of the present disclosure. However, as should be apparent, one skilled in the art will recognize that embodiments of the present disclosure may be incorporated into numerous other assemblies, systems and devices.

The embodiments of the present disclosure may include certain aspects each of which may be present in, or performed through the use of, one or more medical devices, assemblies, or systems thereof. Furthermore, the illustrated exemplary embodiments disclosed herein may include more or less structures than depicted and are not intended to be limited to the specific depicted structures. While various portions of the present disclosure are described relative to specific structures, methods, or processes with respect to a medical device, assembly, or system using specific labels these labels are not meant to be limiting.

A detection scope described herein, as part of a detection system for example, may be part of an existing inspection system utilized at a medical facility. Alternatively, the detection scope or fiber scope may be a proprietary scope. Such detection scopes may be made from any suitable biocompatible material, including but not limited to metals, metal alloys (e.g. stainless steel) and polymers (e.g. polycarbonate), and may be formed using any appropriate process, such as extrusion or milling, screw-machining or molding (e.g. injection molding). Furthermore, detection scope assemblies described or contemplated herein may have any suitable dimensions, such dimensions allowing the detection scope to be positioned within and pass through the various working channels of a medical device being reprocessed, for example.

Reference will now be made in detail to the present exemplary embodiments, which are illustrated in the accompanying drawings.

Figure 1:
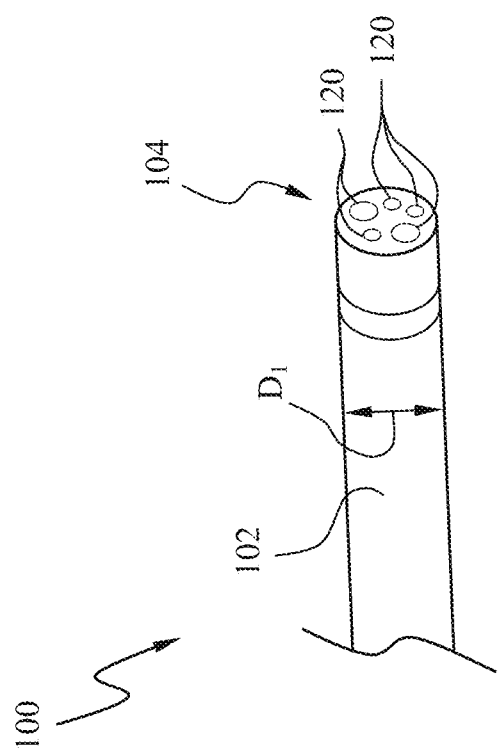
FIG. 1 depicts a side prospective view of an exemplary endoscopic device utilized in medical procedures including one or more working channels.

Turning to FIG. 1, an exemplary medical endoscope or scope 100 utilized in a medical procedure may include an elongate shaft 102, having a diameter $D_1$, terminating in a distal end 104. The medical endoscope 100 may include one or more working channels 120 through which fluids or other medical devices may be communicated or positioned therethrough, respectively, each of the working channels 120 having a respective one of a plurality of diameters. The medical endoscope 100, for example, could be an endoscope utilized in a medical procedure, such as a colonoscope, a laparoscope, a cannula assembly, an arthroscope, an accessory such as arthroscopic shaver component, or the like. Depending upon the type of scope and procedure, exemplary medical devices provided to be transmitted through the one or more working channels 120 may include ablating devices, irrigation devices, and/or tissue sampling devices, to name a few. Such medical devices may contaminate the corresponding one or more working channels 120 with bio-burden, or biological defects, as described above. Additionally, excessive use of the medical devices, or the endoscopic system itself, may result in mechanical defects or non-biological debris being positioned within a portion of the one or more working channels 120 of the endoscope 100.

Figure 2N:
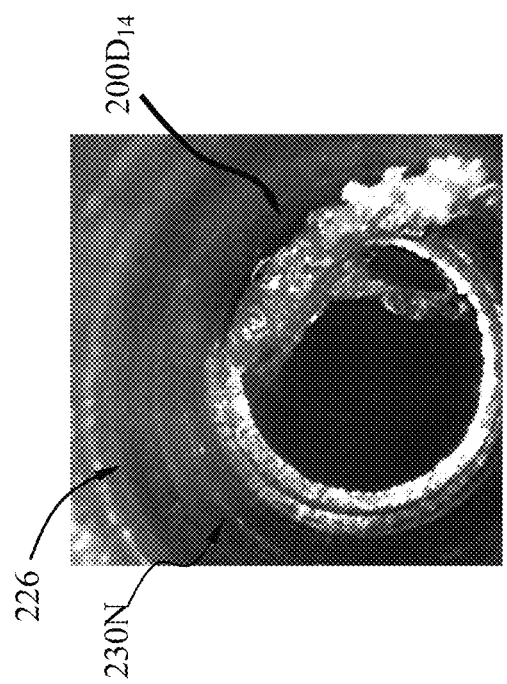
FIGS. 2A-2N depict various examples of defects that may be present in a medical device after a reprocessing procedure.

Turning to FIGS. 2A-2N, examples of various defects, collectively referred to as defects 200D, will be described in greater detail. Once a medical device is utilized in a medical procedure, such as the endoscope 100, the medical device may then be reprocessed in preparation for use in a future medical procedure. FIGS. 2A-2N depict various exemplary defects, collectively referred to as defects 200D, that may be discovered after such a reprocessing procedure. Biological defects may lead to patient infection and/or injury. Mechanical defects may allow microbiological accumulations to take place in areas impossible to clean or decontaminate or may allow biological or non-biological materials to pass through a wall of a surgical instrument, such materials potentially contaminating a patient's body or other portions of the surgical instrument being utilized.

For illustration purposes only, and with specific reference to FIG. 2A, a defect $200D_1$ is depicted being located within a lumen 230A of a surgical instrument 200. The defect $200D_1$ is a metal shard or corrosion present in the lumen 230A. Turning to FIG. 2B, a defect $200D_2$ is depicted in a lumen 230B of a surgical instrument 202, the defect $200D_2$ being diffuse rust and corrosion. FIG. 2C depicts mechanical defects $200D_3$ depicted along a portion of a lumen 220C as part of a arthroscopic shaver 204. Such mechanical defects $200D_3$ may include rust and corrosion produced, for example, through translation of medical devices through the lumen 200C, which may, in turn, result in metal or plastic filings invading the lumen 220C. Mechanical defects 200D3 may also include separation of various elements of the shaver 204, such as metal separation, which may allow for leakage of biological material from one portion of the shaver 204 to another, or into a body cavity of a patient. Disruption of the normal materials or interruption of the surface characteristics associated with various lumens of surgical instruments may provide a lodging point or substrate for an undesirable formation of biofilms and/or microbiological colonies.

Turning to FIG. 2D, foreign material or defect $200D_4$ is depicted near a lumen 230D of surgical instrument 206. FIG. 2E depicts defects $200D_5$, which may include staining and a mechanical defect in the wall of a lumen 230E of a surgical instrument 208, while FIG. 2F depicts dislodged material or defect $200D_6$ from a wall of a lumen 230F of a flexible surgical instrument 210. Now turning to FIG. 2G, mechanical defects $200D_7$ may indicate sever degradation of wall structures associated with a lumen 230G of a flexible endoscope. FIG. 2H depicts a crushed lumen or mechanical defect $200D_8$ in a lumen or working channel 230H of a flexible endoscope 214, and FIG. 2I depicts another structural defect $200D_9$ in a lumen 2301 of a surgical instrument 216.

Figure 2M:
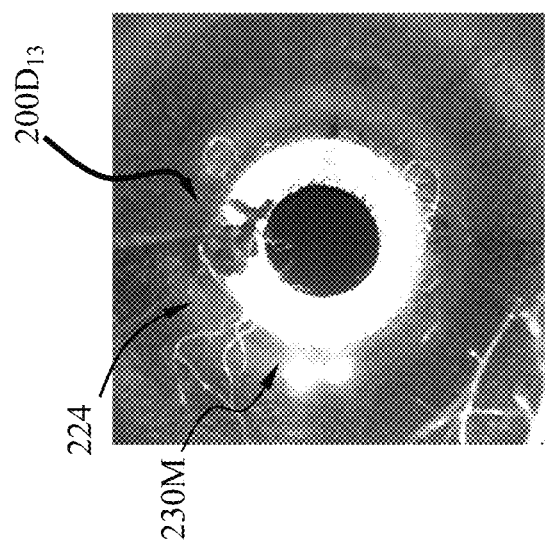

Turning to FIG. 2J, defects $200D_{10}$ are depicted in the form of fluids that may have remained within a lumen 230J of a flexible endoscope 218 after a surgical procedure or a reprocessing procedure. FIG. 2K, as with FIG. 2J, also depicts fluids or defects 200D11 in a lumen 230K of a flexible surgical instrument 220. With reference to FIG. 2L, a defect $200D_{12}$ is located within a working channel or lumen 230L of a medical instrument 222. The defect $200D_{12}$ may be a biological defect such as a hair fiber or may be a non-biological defect such as a clothing fiber, for example. FIG. 2M also depicts fiber defects 200D13 located with a lumen 230M of a medical instrument 224. FIG. 2N depicts foreign material, or defect 200D14, within a lumen 230N of a surgical instrument 226. All of the defects 200D have been discovered after a reprocessing procedure has been performed, and each defect $200D_1$-$200D_{14}$ may result in undesirable patient contamination, patient injury or death during future medical procedures.

Figure 3:
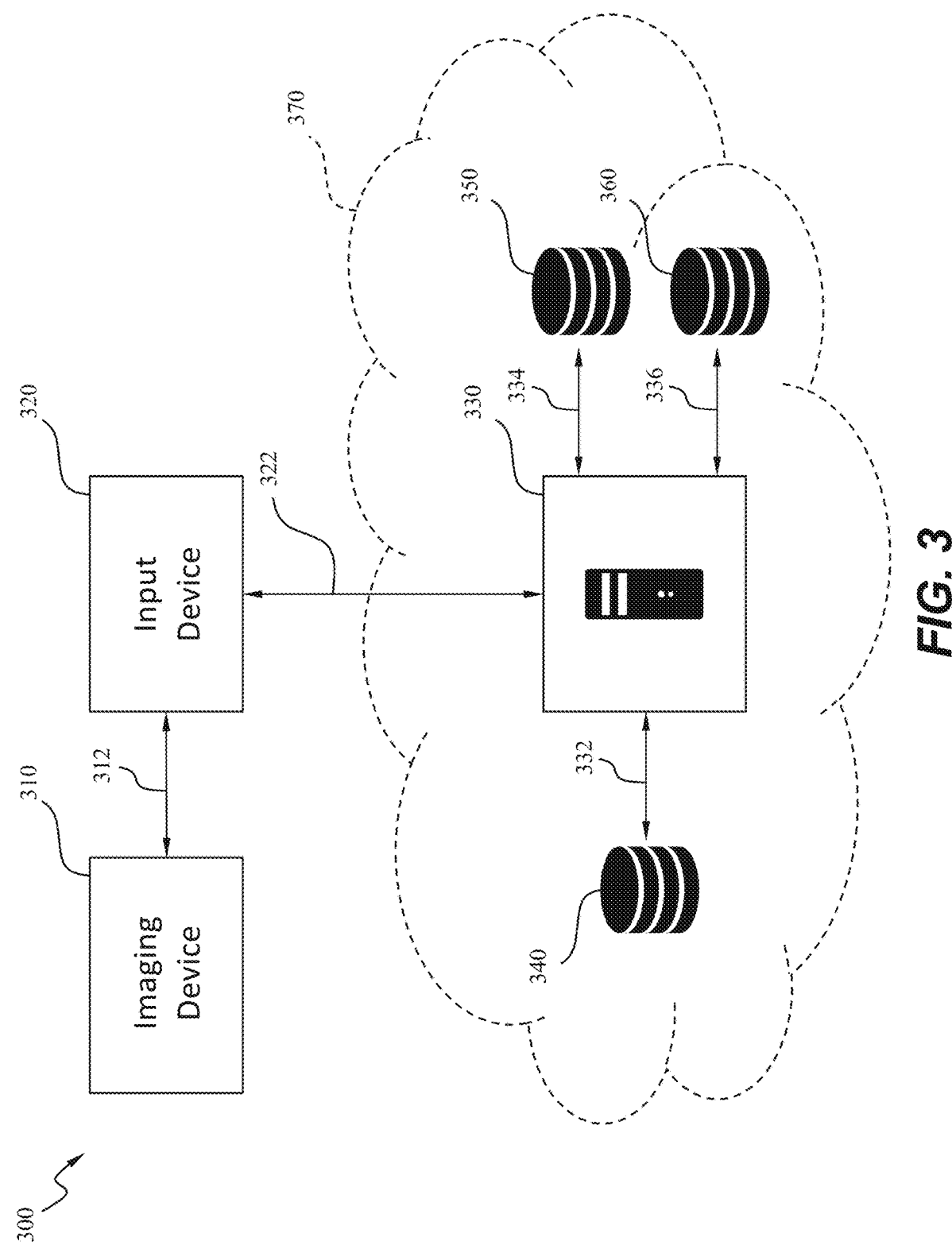
FIG. 3 is a schematic representation of an exemplary detection system.

Turning to FIG. 3, a detection system 300, in accordance with this disclosure, may include an imaging device 310, an input device 320, a processor 330, and one or more data sources, such data sources may include a meta data record (MDR) 340, a Medical Instrument Record (MIR) 350, and a service data record (SDR) 360. The one or more data sources may include sufficient data to allow for a proper analysis and, ultimately, a better determination regarding the inspection and future use of a corresponding medical device or instrument; an increase in the amount of acquired data may directly lead to the better determination.

The detection system 300 may include computer-executable code that allows for obtaining information from and storing information to the one or more of the data sources 340, 350, 360. While depicted as being three separate data sources, the data sources 340, 350, 360 may be part of any number of one or more data sources. Additionally, while the elements of the detection system 300 are depicted being directly connected to the processor 330, such connections may be through wired or wireless communication links, and the locations of each element of the detection system 300 may be local or remote with respect to remaining ones of the elements of detection system 300. For example, the imaging device 310 may be configured to acquire imaging in a room where the reprocessing procedure is taking place, the room being part of a medical facility, and transmit the imaging to a remotely located processor 320, which then communicates associated data, derived from an analysis of the imaging, with the various data sources 340, 350, 360, each being located in a separate location from the processor 330.

Figure 4:
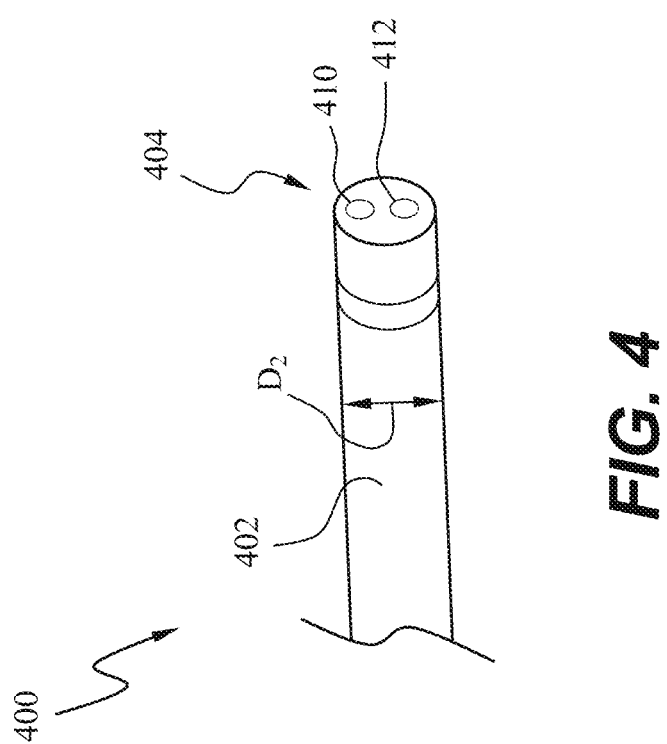
FIG. 4 depicts a side prospective view of an exemplary detection scope, as part of a detection system, in accordance with this disclosure.

The imaging device 310 may have the ability to capture images at a specified rate and transfer the corresponding image data via an input device 320 to the processor 330 for further processing. The image device 310 may include processing of its own such that the image data is preprocessed prior to being provided to the processor 330. Alternatively, the image device 310 may simply provide raw image data to the processor 330, which may provide further processing of the received images. Turning also to FIG. 4, an exemplary imaging device 400 may be one of a plurality of different inspection or fiber scopes, as part of an inspection scope system currently available that can provide imaging data, as discussed below, which then can be digitized for analysis by the detection system 300, for example. The imaging device 400 may be a scope having an elongate shaft 402, which terminates at a distal end 404. The distal end 404 may include a light source 410 and an image sensor 412 to illuminate and capture images while the imaging device 400 is positioned within a working channel of a medical device during a reprocessing procedure, for example. The elongate shaft 402 of the imaging device 400 may be configured to be suitable for being positioned within working channels of medical devices, such as working channels 120 of scope 100. The elongate shaft 402, for example, may have a diameter $D_2$ that is smaller than a diameter of any of the one or more working channels 120 of scope 100. Additionally, the elongate shaft 402 may have a suitable length to be extended through a working channel of a medical device, such as the working channel 120 of endoscope 100. One or more of the light source 410 and image sensor 412 may be located at the distal end 404 of the imaging device 400. Alternatively, either of the light source 410 or the image sensor 412 may be positioned proximal to the distal end 404, or at a proximal end of the elongate shaft 402, in a handle portion, for example. If the light source 410 is positioned proximal to the distal end 404 of the scope 400, light generated by the light source 410 may be transmitted to the distal end 404 through any suitable means, through the use of one or more optical fibers (not shown) positioned within the elongate shaft 402. The one or more optical fibers may terminate at the distal end 404 of the elongate shaft 402 via a lens portion (not shown) that may focus the light in a desired manner.

Additionally, light may be transmitted from the distal end 404 of the elongate shaft 402 to a more proximally positioned image sensor 412 via one or more optical fibers, the one or more optical fibers terminating at the distal end 404 via a lens portion (not shown) configured to collect light provided by the light source 410. The light generated by the light source 410 and obtained by the image sensor 412 may be in the visible range, or may have a wavelength outside the visible range, but is better suited to illuminate and define the inner structures of a medical device being reprocessed. While the light source 410 and image sensor 412 are depicted as being separate elements, they may be formed as a single unit allowing for a smaller diameter $D_2$ allowing the imaging device 400 to be utilized in medical devices having working channels with proportionally smaller diameters.

Alternatively, the methods of this disclosure may be applied to existing scopes utilized by medical facilities in reprocessing procedures, rather than the scope 400. Such existing scopes with adequate image acquisition may be adapted to provide the acquired imaging to the processor 330 of the detection system 300, utilization of the existing scopes reducing associated costs of the medical facility, while increasing the efficiency and accuracy of a reprocessing procedure. If required, the existing scopes of associated inspection systems may be further adapted to provide for image acquisition suitable for use with the detection system 300. For example, an alternative light source may be able to be utilized to increase available light, or a lens portion may be fitted upon a distal end of the existing scope to increase the scope's ability to transmit and receive light.

Turning back to FIG. 3, the imaging device 310 may communicate with the input device 320 over a bidirectional link 312. The bidirectional link 312 may allow for transmission of imaging data from the imaging device to the input device 320 and, ultimately, to the processor 330 for analysis. The bidirectional link 312 may also provide commands to the image device from the input device 320, or the processor 330, such as when to initiate imaging capture, or the rate of movement of the scope through a working channel of a medical device, for example. While depicted as providing transmissions from the imaging device 310 to the input device 320 over link 312, some or all of such transmissions may be communicated directly to the processor over another bidirectional communication link (not shown).

The input device 320 may be any suitable device having the ability to obtain or direct imaging data from the imaging device 310 to the processor 330. The input device 320 may be configured to execute computer-executable code independent of the processor 330. For example, the input device 320 may be a tablet, such as an iPad®, or other computing device, such as a desktop or laptop computer system, allowing an inspection technician to log into the detection system 300 and provide data and command communication therebetween. Once logged into the detection system 300 the technician may initiate an inspection process by instructing the imaging device 310 to start acquiring imaging data. The input device 320 may communicate with the processor 330 over a bidirectional communication link 322. The input device 320, once an inspection technician has logged into the detection system 300, may be configured to receive user interface data from the processor 330. Such user interface data may then be utilized to provide a desired user interface on the input device 320 tailored for that specific inspection technician based upon their login criteria and the specific type of inspection they will be performing. Additionally, imaging data received by the input device 320 from the imaging device 310 may be transmitted to the processor 330 on the communication link 322. As will become more readily apparent in light of the discussion below, the communication link 322 may be utilized to provide additional data, data resulting from analysis of the processor 330, for example, to a user of input device 320, the user being a medical facility risk manager or quality assurance manager, for example, who wishes to see part or all of the data associated with a medical device or instrument. In this case the user interface provided to this user may be different than the user interface provided to the inspection technician for data gathering. Accordingly, the user interface may be different depending on the specific role of the end user at the input device 320. All or part of the functionality of the processor 330 may be provided by the input device 320 itself, as desired by the end user.

The processor 330 may interface to one or more of the data sources 340, 350, 360 prior, during, or after a medical procedure to correlate associated procedure data. Meta data, for example, may be obtained from the MDR data source 340. Such meta data may include, for example, patient data approved by the patient to be part of the data source 340, deidentified patient data, and/or medical data derived from medical studies related to a medical procedure to be performed on a patient, for example. The detection system 300 may obtain deidentified patient data through analysis of patient documents, redacting certain data specific to the patient, including imaging data that may include facial features of the patient. The meta data may include, for example, anomalies in patient biology that would render a specific medical device improper for a given medical procedure due to an increased inflexibility of the medical device over its lifetime, or the existence of excessive wear that would make mechanical failure of the medical device more imminent. For illustration purposes, the detection system 300 may be utilized to analyze meta data and corresponding procedural data, noting a commonality such as a high number of patient readmissions for infection, for example. A further analysis of the data may then determine the medical instrument or instruments utilized for the procedures. The detection system 300 may remove a single medical instrument from further patient use, the medical instrument being determined to likely be the source for infection and, accordingly, unsuitable for performing future medical procedures. Furthermore, an analysis by the detection system 300 may determine that a specific type of medical instruments result in an increase in patient infection due to design constraints, for example, prompting a removal of this specific type of medical instrument from future medical procedures at a medical facility.

The detection system 300 may include computer-executable code that allows for the tracking of the data of the medical devices utilized in corresponding medical procedures, with associated data being stored in a medical instrument record as part of the MIR data source 340. Medical instrument record data may allow technicians, as well as risk managers or quality assurance managers of medical facilities to better monitor the service status of a medical device or instrument from its initial purchase and introduction to the medical facility until its removal from service, providing a complete historical record of all servicing of the medical device. In this way, the detection system 300 may be able to better determine when certain types of mechanical failures of the medical device are imminent, or when the medical device should be removed from service. This may result in fewer intraprocedural stoppages or a reduction of time a patient is under general anesthesia, which may lead to increased patient safety and reduced procedural costs. For example, when a medical device is purchased, initial data regarding the device may be obtained through manual entry by a technician or automatic entry acquired through the use of the detection system 300, resulting in the initial creation of a service record defining a baseline for the medical device from which to compare future medical device data. The data may be associated with the medical device through the use of symbolic identifiers, such as bar codes or device identifiers permanently etched into a portion of the medical device. Such identifiers may be in compliance with the Unique device Identifier (UDI) requirements mandated by the U.S. Food and Drug Administration and the European Union. The medical instrument record may provide a historical record of the use of the associated medical device and may provide technicians or users a more accurate forecast when the medical device should be removed from service, due to excessive wear or mechanical defects, for example.

The detection system 300 may include computer-executable code that allows for the tracking of certain service data, stored as part of the SDR data source 350, related to medical procedures performed at a medical facility, or among a group of medical facilities. Such service data may include the procedure performed, the new or reprocessed medical devices being utilized during the medical procedure, the location of the medical procedure, the surgeon performing the medical procedure, and the medical procedure support staff. By corelating service data with the medical instrument data, as maintained and updated by the detection system 300, a more appropriate medical device may be made available for a given medical procedure. For example, the detection system 300 may schedule the use of a particular medical device for a given medical procedure performed by a particular surgeon, based upon the surgeon's habits and operating style. In this way, the lifespan of a particular medical device may be prolonged, reducing associated product costs of the medical facility.

One or more elements of the detection system 300 may be located remotely, in a data cloud 370, for example. The processor 330 and the data sources 340, 350, 360 may be remotely located with respect to the input device 320 and the imaging device 310. Additionally, the processor 330 and the data sources 340, 350, 360 may be located in the same data cloud 370, such as a server farm located at one physical location, or may be part of one or more data clouds, each located at a different physical location, but together defining data cloud 370. The computer-executed code of the processor 330 may be an application configured to run in the data cloud 370 and exchange data and commands over the bidirectional communication link 322.

Figure 5:
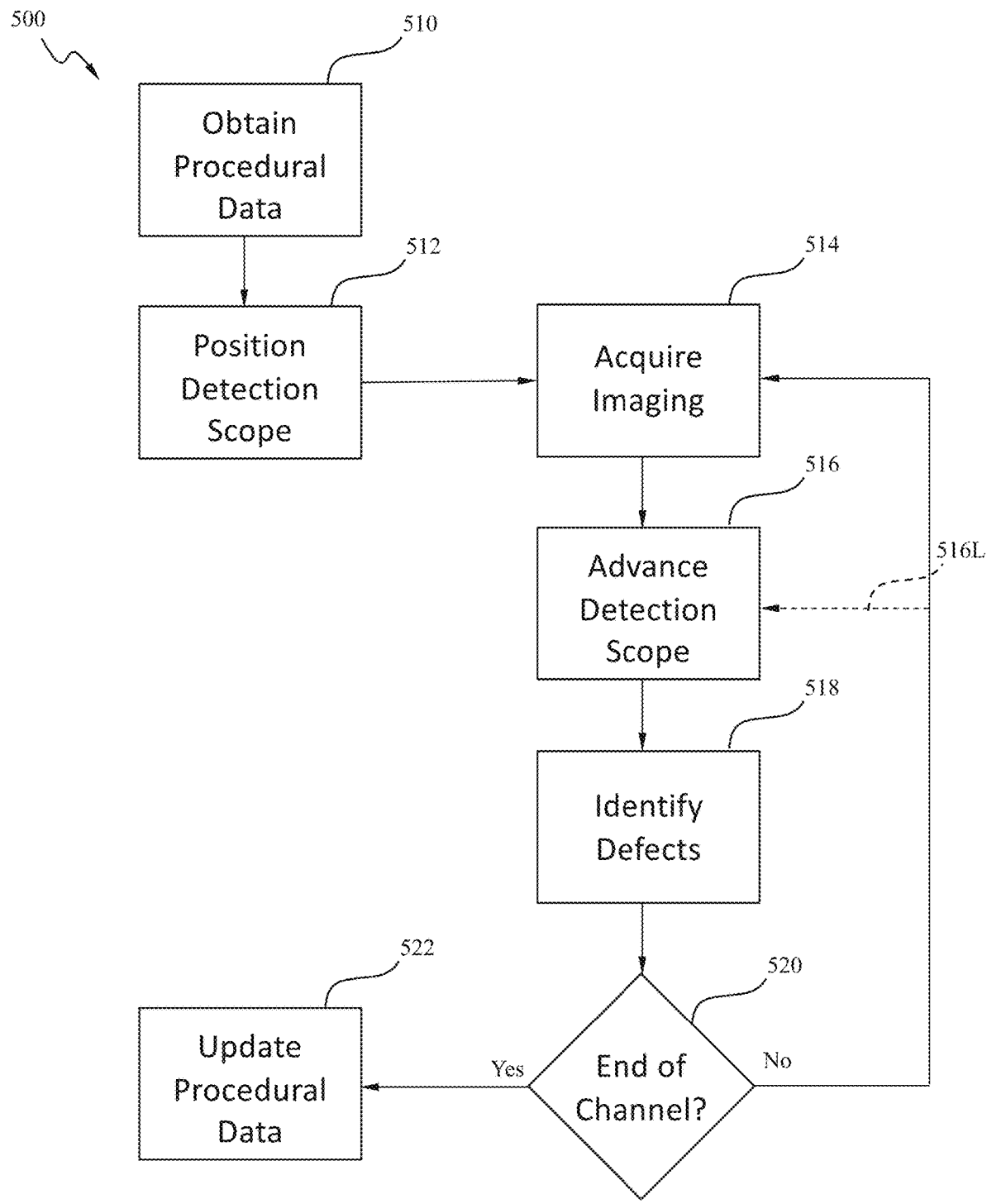
FIG. 5 is a flowchart depiction of an exemplary method, in accordance with the present disclosure.
Figure 6:
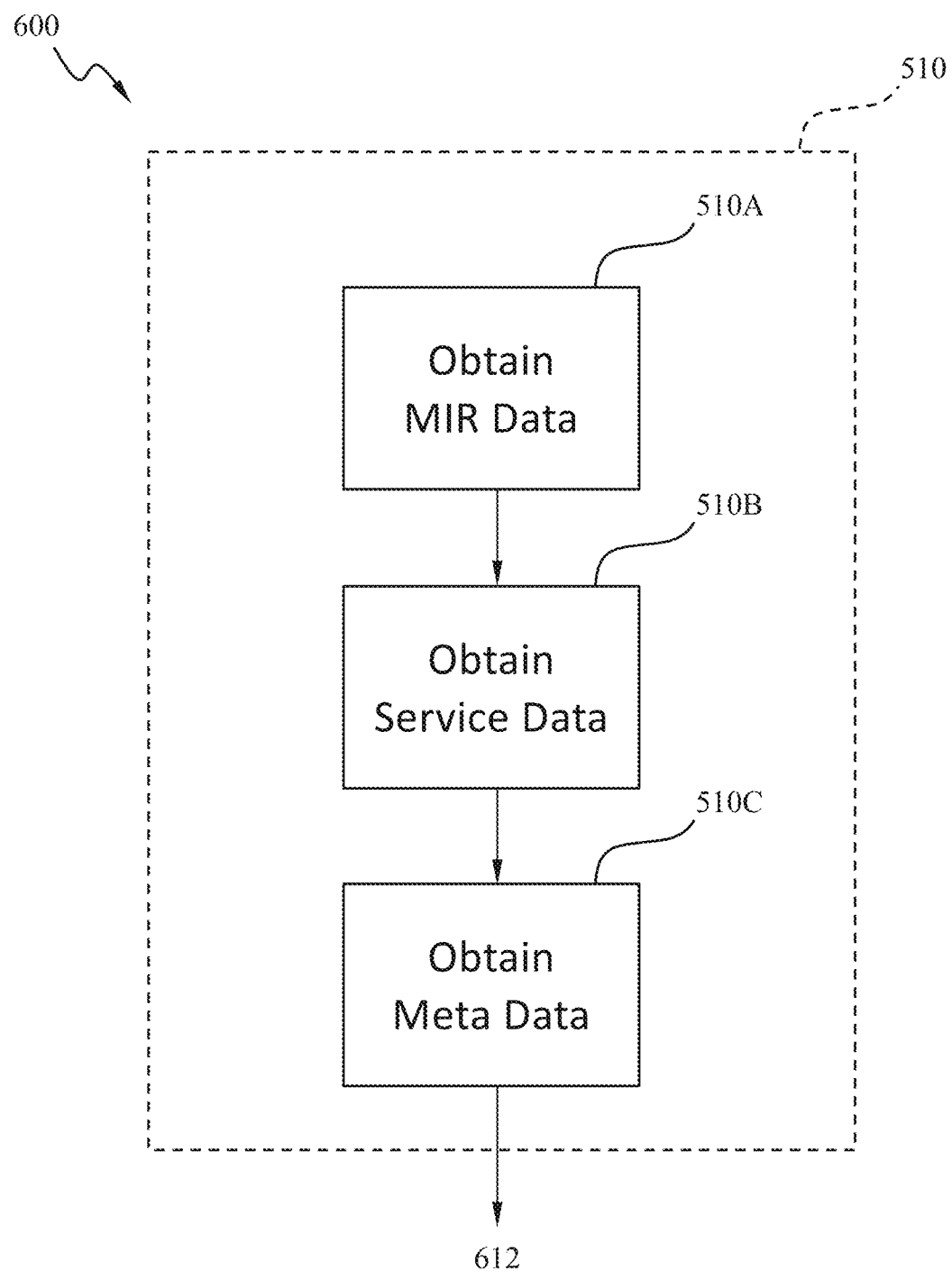
FIG. 6 is a detailed flowchart depiction of a first portion of the exemplary method of FIG. 5.

Turning to FIG. 5, a method 500 in accordance with this disclosure for reprocessing a medical device may include an initial step 510 of obtaining procedural data. Turning momentarily to FIG. 6, a method 600 provides a more detailed depiction of step 510 of method 500. More specifically, the step 510 may include one or more of obtaining MIR data in a step 510A, obtaining service data in a step 510B, and obtaining meta data in a step 510C. Turning back to FIG. 5, the detection scope, such as scope 400 or an existing inspection scope owned by the medical facility, may then be initially positioned within a working channel of the medical device being reprocessed in a step 512. For example, a digital inspection camera may be adapted to be utilized by the detection system 300 as imaging device 310 to obtain images from which the status of the medical device may be determined, the digital inspection camera being positioned within the working channel of the medical device in the step 512.

One or more images may then be acquired by the imaging device, such as device 310, and transmitted to the processor 330, via input device 320 or directly to the processor 330, in a step 514. Multiple images may be taken at a specific location, the detection system 300 being adapted to select a desirable image from the multiple images. Once a desirable image is acquired, the detection scope may then be advanced in a step 516. The advancement of the detection scope may be performed manually or may be provided automatically through the use of a linear actuator (not shown), the control of such advancement of the linear actuator being provided by the input device 320 or the processor 330, or a combination of both. For example, the linear actuator may be utilized to provide for a specified movement over time, e.g., movement at a known rate, which may aide in the image analysis and, ultimately, the determination of biological or mechanical defects that may be present in the working channel of the medical device. Biological or mechanical defects may be identified in a step 518. The processor 330 may include computer-implemented code executed by the detection system 300 that analyzes the acquired images in the step 514, utilizing certain algorithms that may be machine learning or adapted from artificial intelligence.

A determination as to whether the end of the working channel of the medical device is reached may be performed in a step 520. If the end of the working channel is not reached, additional images may be acquired, advancement of the detection scope through the working channel of the medical device, and identification of defects present may be performed through the repetition of steps 514, 516, 518, respectively, until the end of the working channel is reached in the step 520.

Figure 8:
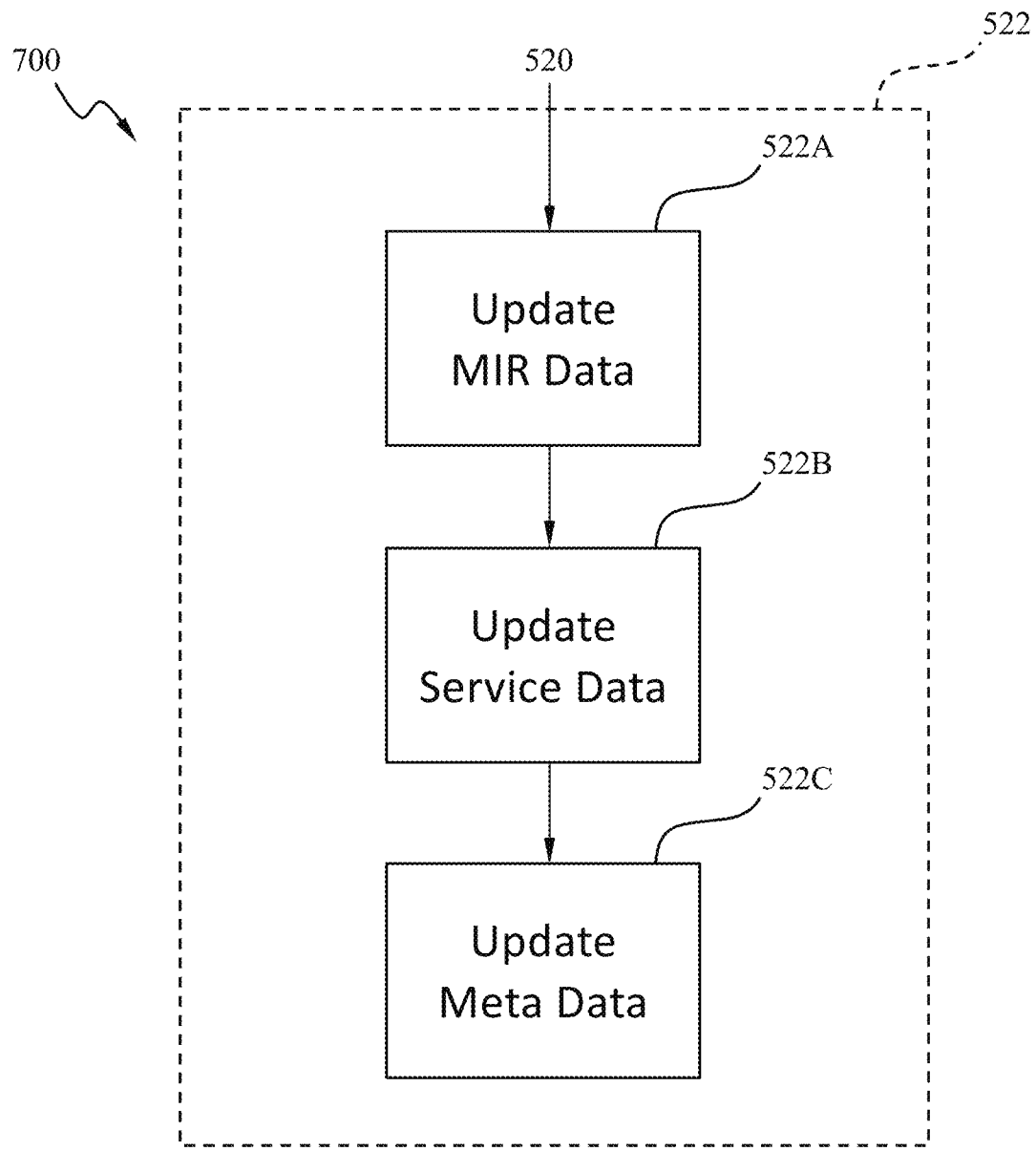
FIG. 8 is a detailed flowchart depiction of a second portion of the exemplary method of FIG. 5.

Once the end of the working channel is reached, procedure data may then be updated in a step 522. Turning briefly to FIG. 8, the step of updating procedure data may include one or more of updating MIR data in a step 522A, updating service data in a step 522B, and updating meta data in a step 522C. For example, updated MIR data may include the presence of defects, biological, non-biological, or mechanical, and/or the extent of wear present in one or more working channels of the reprocessed medical device As described above, such data may be analyzed to provide for better medical device selection for a given patient, surgeon, and medical device, whether the medical device is at its end of life, or whether the medical device should be reprocessed due to the presence of defects.

Figure 7B:
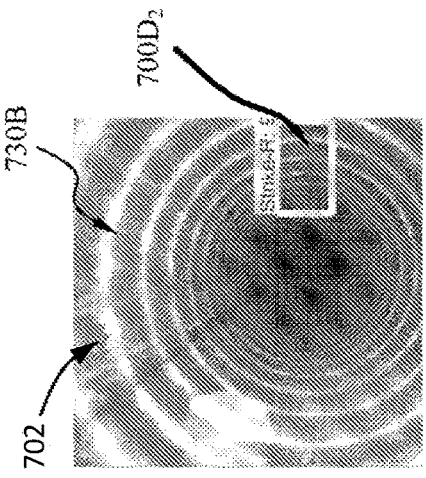
FIGS. 7A-7D depict portions of medical instruments during defect analysis and detection.
Figure 7D:
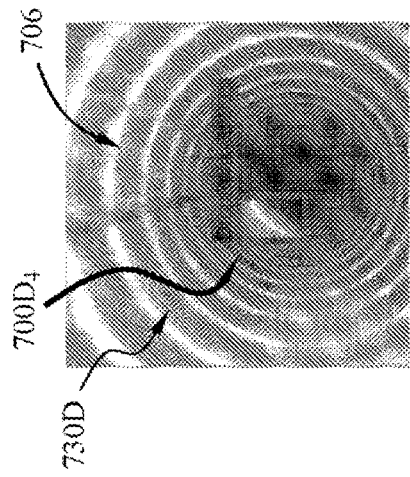
Figure 7A:
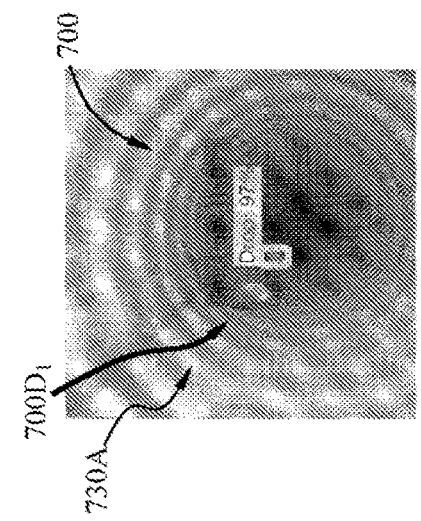
Figure 7C:
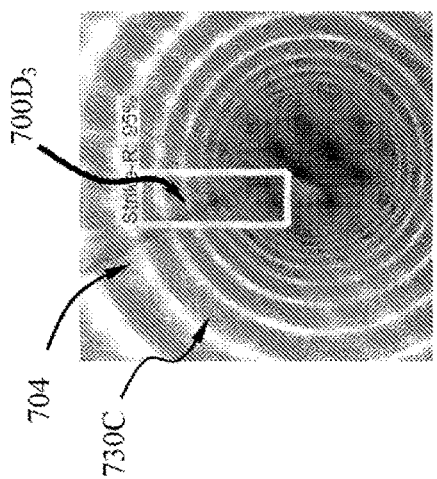

Turning to FIGS. 7A-7D, exemplary defects may be determined by the detection system 300. For illustration purposes, artificial intelligence (AI) may be utilized, as part of the code executable by one or more elements of the detection system 300, to detect and further analyze defects of portions of surgical instruments during a reprocessing procedure. With reference to FIG. 7A, AI may be utilized to analyze imaging received from an inspection camera translating within a lumen 730A of a surgical instrument 700. For example, by comparing certain physical characteristics of the lumen 730A a defect $700D_1$ may be detected. Through further analysis of the imaging associated with the defect $700D_1$, the detection system 300 may further determine that the defect is a liquid or fluid. Turning to FIG. 7B, AI may be utilized to detect mechanical defects, such as defect $700D_2$, which may be a scratch or other anomaly resulting from the passage of traumatic instrumentation through lumen 730B of surgical device 702. Alternatively, the defect $700D_2$ may be the result of a manufacturing anomaly. In either case, the detection system 300 may message the end user to remove the medical instrument 702 from service and/or notify the end user that physician training may be needed to help mitigate such medical device damage in future procedures. As with FIG. 7B, FIG. 7C depicts a mechanical anomaly or defect 700D$_3$ in a lumen 730C of a medical device 704. Once the detection system 300 has detected the defect 700D$_3$, the percentage of wear associated with the lumen 730C can be determined and the remaining lifespan of the medical device 704 can then be calculated. FIG. 7D depicts another instance where a fluid or liquid, e.g., a defect 700D$_4$, is discovered in a lumen 730D of a surgical instrument 706. In this case, the detection system 300 may determine that the medical instrument 706 may be further processed to remove the defect 700D$_4$, the medical instrument 706 then being put back into service. The detection system 300 may be utilized to determine the nature of the defect and, further, the type of substance present, whether biological or non-biological, and the final disposition of the associated medical device or instrument. All historical data associated with a specific medical instrument is stored, as described or contemplated herein.

A more specific location within a medical device of the various defects described above with reference to FIGS. 7A-7D may be determined through the use of various methodologies. One methodology, for example, may be optical flow. The detection system 300 may know the initial position of the imaging device 310 relative to a device being inspected, one or more of the medical devices 702, 704, 706, 708, for example. The detection system 300 may then analyze the collected sequential images received from the imaging device to determine a more specific location of a defect located within the medical device. More specifically, through optical flow techniques the detection system 300 can analyze the progression of images received by the imaging device 310 as the imaging device 310 translates through the medical device, and through optical flow analysis of the objects observed in these images, including defects, a more accurate location of the defect 700D may be more readily. Utilizing optical flow techniques, the detection system 300 may calculate the motion between sequential images, taken at times t and delta t, at every pixel position with respect to the spatial and temporal coordinates of the imaging device 310.

Another methodology may include accelerometry. The detection system 300 may analyze the images, as described immediately above, and calculate a change in position of the distal end of the imaging device 310 over time, from which acceleration can be inferred. Instantaneous velocity, as well as distance, can be determined from this observed acceleration. Position data from the distal end of the imaging device 310 can be combined with data obtained through the optical flow methodology described above to obtain better position data of a defect present in the medical device. Such a process may be performed as part of the code executable by one or more elements of the detection system 300. Alternatively, an accelerometer may be affixed to the distal end of the imaging device 310 for obtaining accelerometer data. The accelerometer data may then be provided to the processor 330, or other processing unit of the detection system 300, to determine velocity and distance data, which then can be combined with the data obtained through the optical flow methodology described above to obtain better position data of a defect present in the medical device.

Another methodology may be translation control of a motor utilized to translate the imaging device 310 through a medical device where there is a known relationship between motor rotation and linear distance traversed by the distal tip of the imaging device 310. For example, the motor may be a stepper motor with specific control over translation where upon a command the motor drive shaft rotates a known amount that directly corresponds to a known linear distance the imaging device 310 translates. Accordingly, once the imaging device is positioned at a known initial position within the medical device a future translational position may be determined through the translation control of the motor and, ultimately, the location of the distal end of the imaging device 310 and a defect it may be observing may also be known. Data obtained through the use of this methodology may be used in combination with one or more other methodologies to improve the determination of a defect location.

Once the defect detection and analysis are performed by the processor 330 of the detection system 300, a user may log into the detection system 300 via an input device, such as a tablet or computer system, and access the data associated with their particular medical facility. An inspection technician, a risk manager, or quality assurance manager can access the detection system 300, e.g., processor 330, and request medical device data in accordance with their title and search criteria. For example, a risk manager may request to see medical device data associated with all scopes of a particular type for a given time period, e.g., all colonoscopes for the current calendar year. Alternatively, the user can request to see all scope types for all time periods. Still, the user can request to see only those scopes that have experienced mechanical defects or certain amounts of wear associated with usage. The data may be accessed by various fields such as by a medical facility department, a type of instrument, or an amount of mechanical data related to fatigue or wear. Accordingly, quality assurance or quality management personnel of a medical facility can review data in real-time and be audit-ready everyday such that when an audit of the medical facility does occur, the associated medical device data is readily available. At the time of the audit limited access can be provided to the auditor by the medical facility in order to direct the desired data to the auditor in support of the audit being performed, allowing the medical facility personnel to be more productive while providing a more efficient audit experience. In this way, managerial staff of the medical facility can be prepared, with little or no notice, for upcoming audits, being able to provide auditors desired data in support of the audit at the click of a button without having to go through a plethora or paper documents.

Turning back to FIG. 5, the step 514 of acquiring imaging may include the step of continuously acquiring imaging. Accordingly, once continuous imaging is being acquired, the detection scope may then be advanced in the step 516 and defects may be identified in the step 518, and if the working channel has not been reached the steps 516, 518 of advancing the detection scope and identifying defects in the working channel may be performed in a loop until the length of the working channel is reached, as indicated by dashed line 516L. In any case, since defect identification is performed in real-time a technician or other worker supervising the reprocessing procedure may be immediately notified when a defect is identified, prompting the technician to review or note such defects. Alternatively, it should be readily apparent that while defect identification is being performed simultaneously with advancement of the detection scope in the depicted method 500, the step 518 of identifying defects may be performed at a later time. For example, the step of defect identification may be performed through image analysis after the end of the working channel has been reached by the detection scope.

Data associated with the reprocessing procedure may become part of one or more of the data sources 330, 340, 350. Such data may include the one, some, or all of the images acquired, the rate at which the detection scope is advanced through the working channel of the reprocessed medical device, and the type and nature of the defects identified. For example, mechanical wear may be obtained and analyzed such that an informed decision may be made regarding the lifespan of the medical device or whether the medical device should be removed from service. The acquired images may be obtained as individual images or a collection of images, as part of a video. Such images may be processed to increase the contrast of the walls of the working channel, allowing for better defect detection.

It should be understood, features of any one of the above-described embodiments described herein may be applied to any other of the above-described embodiments, as appropriate. The devices contemplated or described herein may be made from any suitable biocompatible material, including but not limited to metals, metal alloys (e.g., stainless steel or nitinol) and polymers (e.g., polycarbonate or Teflon™).

The invention claimed is:

1. A method for detecting defects of a medical device, the method comprising:
analyzing, based on operation of one or more processors of a detection system, a plurality of images;
detecting, by the operation of the one or more processors of the detection system, a plurality of different defects comprising one or more liquids, biological debris, non-biological debris, contaminants, and mechanical defects in the plurality of images using an artificial intelligence technique in conjunction with said analyzing;
positioning a detection scope within the medical device;
acquiring one or more images at a current location of the detection scope;
detecting, by the operation of the one or more processors of the detection system, one or more of the plurality of different defects within the medical device using the artificial intelligence technique, wherein detecting the one or more defects comprises:
determining the one or more defects to be a particular liquid, biological debris, non-biological debris, contaminant, or mechanical defect based on said analyzing;
obtaining first data comprising a record of one or more issues experienced by a plurality of patients after undergoing a procedure that involved the medical device;
obtaining second data comprising a service history of the medical device; and
selecting the medical device for reprocessing, removal from service, or a next procedure based on the first data, the second data, and the one or more defects.

2. The method of claim 1, wherein said positioning of the detection scope comprises:
positioning the detection scope within a working channel of the medical device.

3. The method of claim 2, further comprising:
determining whether an end of the working channel of the medical device has been reached;
advancing the detection scope;
repeating steps of acquiring the one or more images, detecting the one or more of the plurality of defects, and determining whether the end of the working channel of the medical device has been reached; and
updating procedural data after the end of the working channel of the medical device has been reached.

4. The method of claim 1, wherein said detecting the one or more defects comprises:
determining a location for each of the one or more defects.

5. The method of claim 4, wherein said determining the location for each of the one or more defects comprises:
performing an optical flow analysis.

6. The method of claim 4, wherein said determining the location for each of the one or more defects comprises:
measuring an acceleration of a distal tip of the detection scope.

7. The method of claim 4, wherein said determining the location for each of the one or more defects comprises:
measuring a ratio between a rotational movement of a motor and a linear movement of the detection scope.

8. The method of claim 1, further comprising:
calculating a remaining useful life of the medical device based on the first data, the second data, and the one or more defects; and
removing the medical device from service based on the remaining useful life.

9. The method of claim 1, further comprising:
tracking usage of the medical device in different medical procedures by different personnel;
identifying a plurality of future procedures scheduled by different personnel; and
scheduling use of the medical device by a particular personnel in at least one of the plurality of future procedures based on the usage and said tracking.

10. The method of claim 1, further comprising:
determining historic usage of the medical device as part of a particular medical procedure from one or more of the first data, the second data, or third data;
scheduling use of the medical device to an upcoming instance of the particular medical procedure based on the historic usage.

11. The method of claim 1, further comprising:
determining a current state of the medical device based on the one or more defects;
tracking historical usage and maintenance associated with the medical device as part of one or more of the first data and the second data; and
determining a remaining useful life for the medical device based on the current state and the historical usage and maintenance.

12. The method of claim 1, wherein said detecting the one or more defects further comprises:
presenting a visual border around one or more regions in the one or more images with the one or more defects.

13. The method of claim 12, wherein said detecting the one or more detects comprises:
presenting a textual identifier adjacent to the visual border, wherein the textual identifier comprises a value associated with the one or more defects within the visual border.

14. The method of claim 1, further comprising:
tracking an extension of the detection scope through the medical device;
associating each image of the one or more images to a different position within the medical device based on a time each image is taken and the extension of the detection scope at the time each image is taken; and providing a specific location of each of the one or more defects within the medical device based said associating.

15. The method of claim 1, further comprising:
activating an optical fiber of the detection scope; and
illuminating a lumen within the medical device with the optical fiber as part of said acquiring the one or more images.

16. A device, comprising:
an imaging device configured to acquire image data; and
a processor coupled to the imaging device, the processor configured to:
   analyze a plurality of images;
   detect a plurality of different defects comprising one or more liquids, biological debris, non-biological debris, contaminants, and mechanical defects in the plurality of images using an artificial intelligence technique in conjunction with said analyzing;
   track a position of the imaging device within a medical instrument;
   acquire one or more images from the imaging device at different locations within the medical instrument;
   detect one or more of the plurality of different defects within the medical instrument using the artificial intelligence technique, wherein detecting the one or more defects comprises:
      determining the one or more defects to be a particular liquid, biological debris, non-biological debris, contaminant, or mechanical defect based on said analyzing;
   obtain first data comprising a record of one or more issues experienced by a plurality of patients after undergoing a procedure that involved the medical instrument;
   obtain second data comprising a service history of the medical instrument; and
   select the medical instrument for reprocessing, removal from service, or a next procedure based on the first data, the second data, and the one or more defects.

17. The device of claim 16, wherein the imaging device comprises:
one or more optical fibers extending to a distal end of the imaging device, wherein the one or more optical fibers are configured to illuminate an inner structure of the medical instrument as part of said acquiring the one or more images.

* * * * *